United States Patent [19]
Fry
[11] Plant 4,770
[45] Sep. 29, 1981

[54] MUSCADINE GRAPE

[76] Inventor: Byard O. Fry, 612 Terrace St., Griffin, Ga. 30223

[21] Appl. No.: 701,793

[22] Filed: Jul. 1, 1976

[51] Int. Cl.[3] ..... A01H 5/03
[52] U.S. Cl. ..... Plt./47
[58] Field of Search ..... Plt./47

*Primary Examiner*—Robert E. Bagwill
*Attorney, Agent, or Firm*—Stanley L. Tate

[57] ABSTRACT

A new variety of Muscadine which is very vigorous, with large fruit of a dark red color, which occurs in large clusters of from 10 to 20 berries, each berry having a diameter of about 0.8 inches; the individual berries having a sugar content of from about 19.5 to about 22.5 percent and producing a fruit yield of from about four (4) to about five (5) tons per acre.

1 Drawing Figure

DESCRIPTION OF THE VARIETY

The new and distinct variety of muscadine grape which is the subject of the present application was originated by crossing the unnamed seedling 42-28 with unnamed seedling 46-32, the former being the seed parent and the latter being the pollen parent.

The general objective of the breeding was to produce an improved variety of muscadine grape plant, the fruit of which would have a higher sugar content than either parent, mature in mid-season, have a vigorous and attractive plant habit, good disease resistance and produce high fruit yields. The new and distinct variety of muscadine, herein described and claimed, meets all of the aforesaid requirements, all of which distinguish it from its parents, as well as from all other varieties of muscadine grape of which the applicant is aware.

In comparison, with both the seed and pollen parents, the new variety produces fruit which is considerably larger and sweeter than the fruit of either parent. The fruit of the present variety contains on an average of from about 19.25 to about 22.5 percent soluble sugar, which sugar content is higher than the sugar content of the fruit of either parent. Further the fruit of the present variety is a beautiful dark red color which is not found in the fruit color of either parent. Also, the present variety yields on the average from about four (4) to about five (5) tons of fruit per acre.

Asexual reproduction of the new variety by layering as performed at Brooks, Ga., shows that the foregoing characteristics and distinctions come true to form and are established and transmitted through succeeding propagations.

The accompanying photograph shows a typical specimen of the vegetative growth and fruit of the new variety when the fruit is ripe and ready for picking and as depicted in color as nearly true as it is reasonably possible to make the same in color illustration of this character.

The following is a detailed description of the new variety.

Species: *Vitis rotundifolia.*
Type: Vine.
Seed parent: Seedling 42-28.
Pollen parent: Seedling 46-32.
Propagation: Holds its distinguishing characteristics through succeeding propagations by layering.
Locality where grown and observed: Brooks, Ga.

Fruit borne: Usually in large clusters of from 10 to 20 berries.
Fruit size: Large, similar in size to seed parent, about 0.8 inches in diameter.
Fruit color: Greyed Red Group 178 B — Fan 4.
Fruit maturity: September 15 to October 15 at Brooks, Ga., and depending upon seasonal conditions.
Sugar content, individual berry: 19.5 to 22.5 percent.
Fruit shape: Uniform round.
Seeds:
- *Average diameter.*—5/32 inches.
- *Average seeds per berry.*—3.90.

Pulp:
- *Color.*—Light green color group 59-B, Royal Horticultural Society, London, England.
- *Consistency.*—Soft and juicy when compared to other muscadine varieties.

Skin: Adheres to pulp.
Foliage:
- *Leaf color.*—Green reading 137-B on The Royal Horticultural Society, London, England, color chart.
- *Leaf size and shape.*—Similar in size and shape to leaves of other muscadine varieties.

Reproductive organs: Pistillate, not self pollenating.
Growth:
- *Habit.*—Vine, requires support.
- *Growth.*—Very vigorous when compared to other varieties grown under similar conditions at Brooks, Ga.
- *Canes.*—Heavy caliper.

Disease resistance: Very good resistance to mildew and black rot as compared to other varieties grown under comparable cultural conditions at Brooks, Ga.

This description was made from a muscadine vine of the new variety bearing ripe fruit in mid September at Brooks, Ga.

What is claimed is:

1. The new and distinct hybrid plant variety of the muscadine as described and illustrated which is primarily distinguished as to novelty by the unique combination of a very vigorous vine, large fruit of a dark red color, said fruit occurring in large clusters of from about 10 to 20 berries, an individual berry diameter of about 0.8 inches, an individual berry sugar content of from about 19.5 to about 22.5 percent, and producing a crop yield of from about four (4) to about five (5) tons per acre.

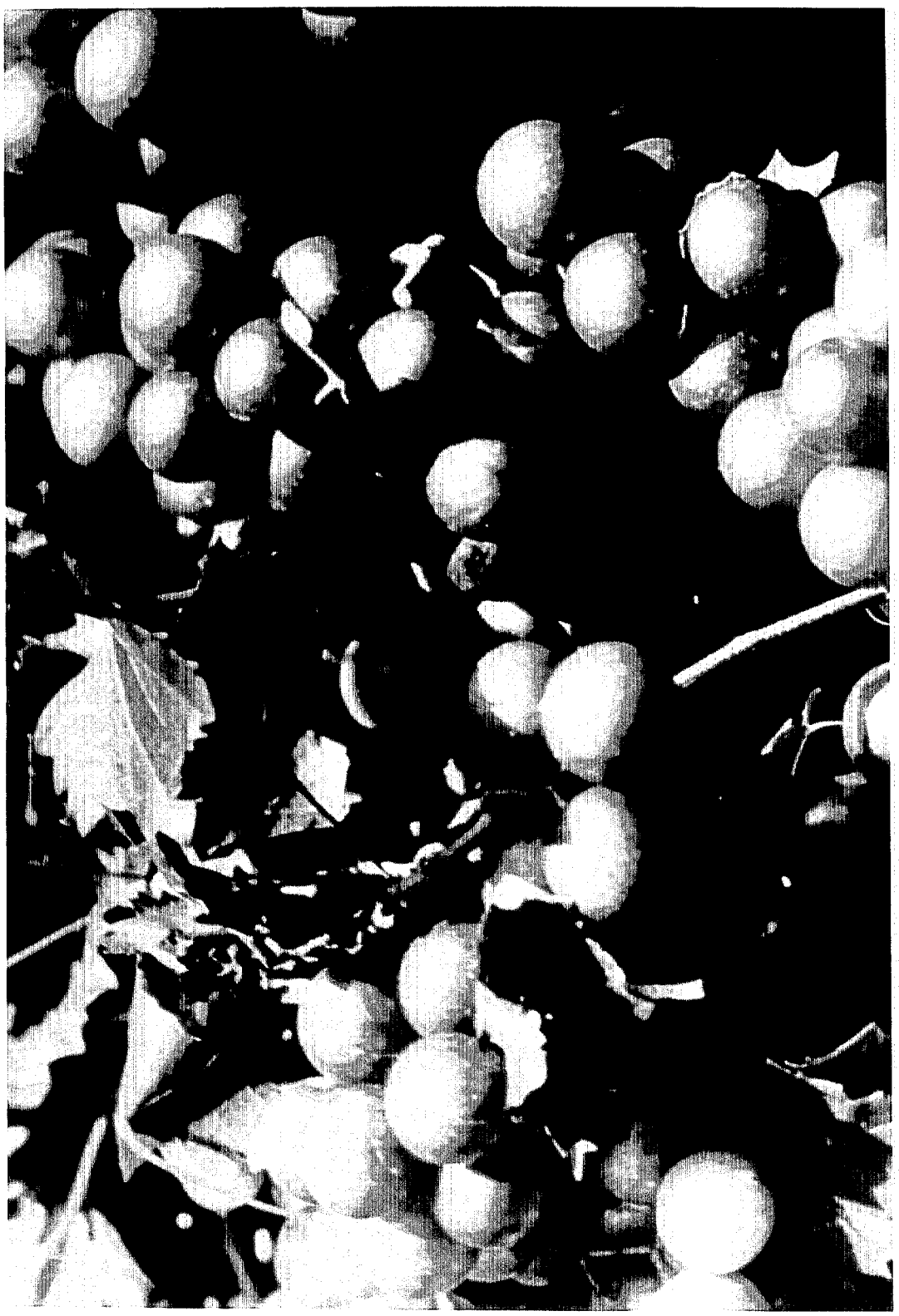

* * * * *